United States Patent
De Luca et al.

(10) Patent No.: US 6,610,538 B2
(45) Date of Patent: Aug. 26, 2003

(54) RECONSTRUCTED LAMINAE OF HUMAN EPITHELIUM CORNEAE AND METHOD OF PRODUCING THE SAME

(75) Inventors: Michele De Luca, Ardea (IT); Graziella Pellegrini, Ardea (IT)

(73) Assignee: Provincia Italiana della Congregazione dei Figli dell' Immacolata Concezione - Istituto Dermopatico dell' Immacolata, Rome (IT)

(*) Notice: Subject to any disclaimer, the term of this patent is extended or adjusted under 35 U.S.C. 154(b) by 113 days.

(21) Appl. No.: 09/961,314

(22) Filed: Sep. 25, 2001

(65) Prior Publication Data

US 2003/0027333 A1 Feb. 6, 2003

(30) Foreign Application Priority Data

Aug. 3, 2001 (IT) ...................................... RM2001A0476

(51) Int. Cl.[7] ........................... C12N 5/08; A61K 35/32; A61K 38/00; A01N 37/18; C07K 1/00; C07K 14/00; C07K 16/00
(52) U.S. Cl. ........................ 435/368; 435/325; 435/363; 435/366; 435/395; 424/574; 424/520; 424/570; 514/2; 514/21; 530/350; 530/382; 530/384
(58) Field of Search ........................ 206/438; 435/307.1, 435/368, 1.3, 371, 374, 456; 424/574; 514/2, 21

(56) References Cited

FOREIGN PATENT DOCUMENTS

| | | |
|---|---|---|
| EP | 0 572 364 | 12/1993 |
| WO | WO 96/13974 | 5/1996 |
| WO | WO 99/37752 | 7/1999 |

OTHER PUBLICATIONS

Tseng (Jan. 1996) "Regulation and Clinical Implications of Corneal Epithelial Stem Cells." Molecular Biology Reports 23(1): 47–58.*
Sangwan (Aug. 2001) "Limbal Stem Cells in Health and Disease." Bioscience Reports 21(4): 385–405.*
Pellegrini et al., "Location and Clonal Analysis of Stem Cells and Their Differentiated Progeny in the Human Ocular Surface", The Journal of Cell Biology, vol. 145, No. 4, May 17, 1999, pp. 769–782.
Pellegrini et al., "p63 identifies keratinocyte stem cells", Proceedings of the National Academy of Sciences of the United States, vol. 98, No. 6, Mar. 13, 2001, pp. 3156–3161.
Rama et al., "Autologous fibrin–cultured limbal stem cells permanently restore the corneal surface of patients with total limbal stem cell deficiency", Transplantation (Baltimore), vol. 72, No. 9, Nov. 15, 2001, pp. 1478–1485.

* cited by examiner

Primary Examiner—Gary Kunz
Assistant Examiner—Christopher James Nichols
(74) Attorney, Agent, or Firm—Young & Thompson

(57) ABSTRACT

A method of reconstructing laminae of human epithelium corneae in vitro to be used in grafts from cultures of limbar stem cells as well as a method of selecting and transferring such cells to fibrin substrate.

12 Claims, 2 Drawing Sheets

RECONSTRUCTED LAMINAE OF HUMAN EPITHELIUM CORNEAE AND METHOD OF PRODUCING THE SAME

The present invention relates to the grafts in the oculistics and more particularly the production in vitro of laminae of human epithelium corneae containing stem cells from cultured limbar stem cells to be grafted directly to patients.

As known, stem cells of epithelium corneae are confined to the layer between cornea and conjunctiva, so-called limbus, and allow the upper layers to be continuously renewed.

In the severe ocular burns the loss of corneal tissue and the total or subtotal depletion of the limbar cells causes the missing epithelium to be replaced by the conjunctival cells forming naturally an opaque layer that causes the loss of sight.

The grafts of tissue portions formed of limbar cells allows the functionality of cornea to be recovered, the blindness due to the destructive lesion of the limbar-corneal epithelium to be overcome, and the perforating keratoplasty to be successfully carried out even in most complex cases where the number of successful results by using the known methods of the state of art is extremely small.

It is known that epithelial cells are difficult to be prepared and kept in vitro as they are fragile and hard to handle so that the methods used hitherto to produce tissues in vitro are little effective.

The present invention seeks to select effectively the limbar cells to be cultivated in vitro and to improve the method of cultivating the same on a fibrin substrate suitably modified to obtain reconstructed laminae of epithelium corneae ready to use in grafts. The human anterior ocular surface is covered with two highly specialized structures: conjunctive and cornea. The function of cornea is to refract light and to direct it to the visual perception region of retina and is responsible for focusing the images along with crystalline. The conjunctive covers the remaining *bulbi oculi* portion and performs an important function in keeping the normal homeostasis of the ocular surface. Although the conjunctival and limbar-corneal tissues have the typical characteristics of the epithelia, they are formed by two genotipically different cell types, hereafter referred to as conjunctival keratinocytes and limbar-corneal keratinocytes, respectively. In particular, epithelium corneae is renewed constantly and continuously because of the stem cells confined in the deepest transitional layer between cornea and conjunctive, so-called limbus, where the transient amplifying cells (TA cells) forming the epithelium corneae are originated. Epithelium corneae is completely renewed every 9–12 months.

The reconstruction in vitro of the epithelial tissue aiming at repairing and/or replacing those natural, for example, as a result of severe burns is widely supported with documents. Cells are cultivated in vitro on suitable biological substrates helping the cell adherence and proliferation as well as allowing the proper architecture of the epithelial tissue to be obtained. One of the most used substrate is fibrin which is available even in commercial form as TISSUCOL (by Baxter-Immuno, Vienna, Austria), a solution of two components: fibrinogen and thrombin. Such composition prepared according to the protocol provided by the manufacturer, however, is not suitable to be used in cultures of limbar-corneal keratinocytes as it is not transparent and elastic enough.

The present invention overcomes the problems relative to the preparation of homogeneous, steady cultivated corneal stem cells. Such cells growing on a suitably modified fibrin substrate originate in vitro laminae of epithelium corneae having all of the characteristics of the human cornea such as size, thickness and transparency. In addition, such method allows such elastic laminae of epithelium corneae to adhere perfectly to the ocular surface without having to cause it to bend during the development in vitro (as described by the same inventor in his Italian Patent No. RM9200408). Therefore, the laminae of human epithelium corneae produced in vitro according to the present invention are ready to use and adapted to any patient.

One object of the present invention is a method by which it is possible to prepare in laboratory laminae of human epithelium corneae to be used in grafts. Such method requires a number of steps to obtain homogeneous cell cultures containing stem cells and capable of easily forming in vitro laminae of human epithelium corneae ready to use because of the modified fibrin substrate.

Further features and advantages of the invention will be more readily apparent from the following detailed description of an embodiment with reference to the accompanying drawings.

PREPARATION OF CELL CULTURES

As described above the cells assigned to the continuous renewal of the epithelium corneae are the cells of the limbar layer also containing stem cells and capable of regenerating all over again the whole epithelium as such. The preparation of cultures of such cells in vitro is carried out according to a new protocol, the object of the invention, including the following steps:

1. Selection of the Cells Taken from Limbus.

Cell samples are taken from the limbar ocular region by biopsy. As mentioned above, limbus is referred to as a transient layer between conjunctival epithelium and epithelium corneae. For this reason, in order to provide cultures mainly formed of corneal cells it is necessary to distinguish the two cell types. Specific markers allow the corneal cells to be distinguished genotipically from the underlying conjunctival cells. It is known that the conjunctival epithelium produces cytokeratin 19, while the epithelium corneae produces specifically cytokeratin 3 and 12.

Therefore, the cell cultures from the biopsy are subjected to an immunotest with specific antibodies for cytokeratin 3 and cytokeratin 19 by a known technique.

Figure 1:
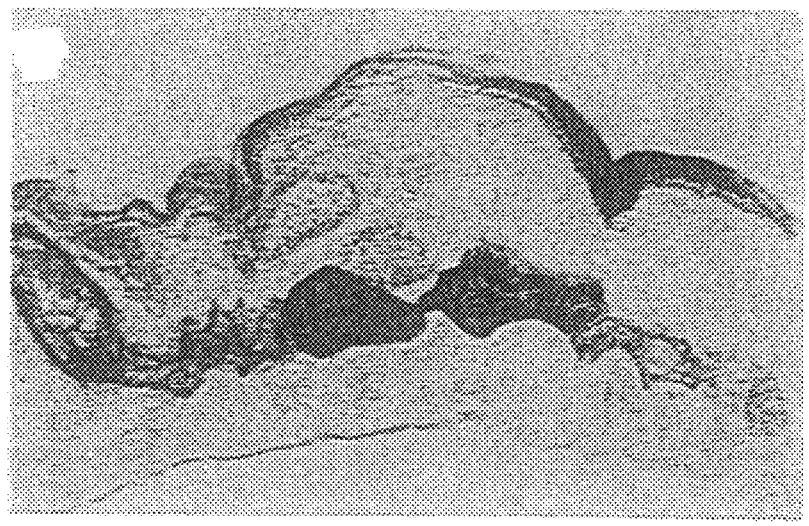
FIG. 1 shows the histologic section of a layer of cells taken from the limbar region, fixed and coloured with specific antibodies K3 and K19.
Figure 2:
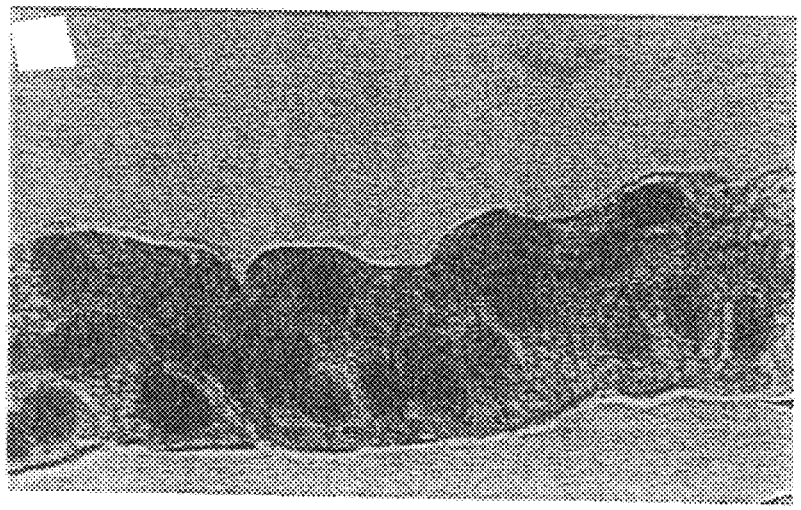
FIG. 2 shows the histologic section of a layer of conjunctival cells fixed and coloured with specific antibodies K3 and K9.

FIGS. 1 and 2 show different cell preparations that react to specific antibodies. In particular, FIG. 1 shows the phenotype K3+/K19− of the corneal cells, while FIG. 2 shows the conjunctival cells with phenotype K3−/K19+. Thus only cultures infected by conjunctival cells by a proportion lower than 50% can be selected, such cultures containing corneal cells with phenotype K3+ and negative cells for specific markers K3 and K19, thus providing as a result cultures containing corneal stem cells.

After having provided preparations mainly formed of corneal and limbar cells with a proportion greater than 50%, it is necessary to find out corneal stem cells.

2. Selection of the Limbar Cells by Clonal Analysis.

As described above, the limbar stem cells originate transient amplifying cells (TA) which differentiate definitively after a number of cellular divisions.

The clonal analysis allows the stem cells to be found out exactly in order to check their presence in the culture. Therefore, cells are sorted as holoclones, meroclones, and paraclones by this technique.

Holoclones are formed by cells with high proliferative capacity which divide about 100 times and belong to the basal limbus layer, and are characterized in that they are able to generate a mature epithelium in vivo and to differentiate. Holoclones are generated by stem cells of limbus [Pellegrini, G. et al., 1999, J. Cell Biol., 145, 769–782].

Paraclones are formed by TA cells that divide 15 times as a maximum and originate colonies formed by cells at the terminal stage of differentiation.

Meroclones are formed by young TA cells which keep a proliferative capacity greater than paraclones. The transition from holoclones to meroclones and paraclones is an unidirectional process.

Figure 3:
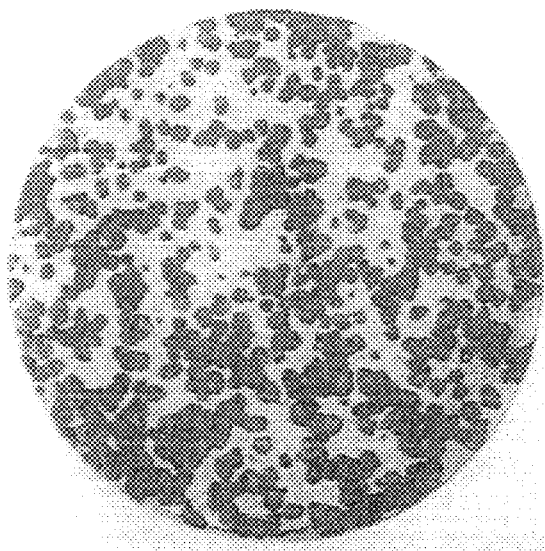
FIG. 3 shows the clones obtained by bioptic samples of the limbar region.
Figure 4:
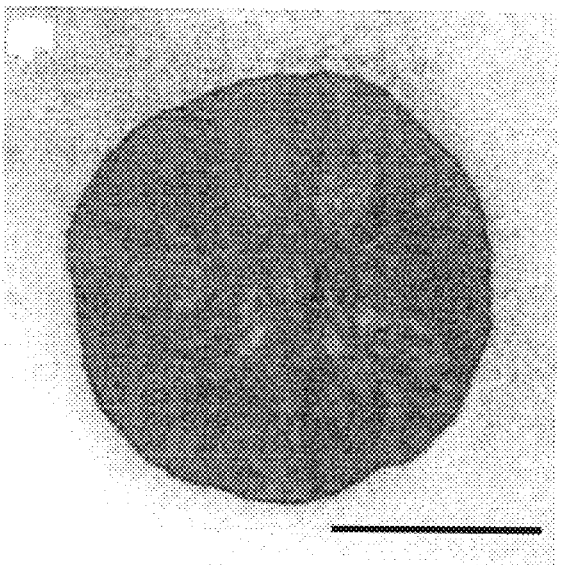
FIG. 4 shows the morphological aspect of a holoclone.

As shown in FIGS. 3 and 4, only cells taken from limbar region are capable of producing large, smooth colonies, the holoclones, and can be cultivated by about 14 passages (2–3 months) and undergo 80–100 cellular divisions before going into senescence.

3. Selection of the Limbar Stem cells by specific markers for limbar cells.

According to the present invention the results provided by the clonal analysis have to be confirmed univocally by further analysis carried out by using specific markers for limbar cells.

Protein p63, a transcription factor of the protein family to which p53 and p73 belong, is used as specific marker [Pellegrini, G. et al., 2001, Proc. Natl. Acad. Sci. USA, 98, 3156–3161]. As known, p53 plays an important role in the fight against tumours, while p63 and p73 are involved in the cellular differentiation process.

The results have pointed out that the presence of p63 in the holoclone cells, i.e. stem cells, is 200 times greater than in the paraclone cells.

Another test of the specific presence of p63 in the stem cells is provided by comparing the levels of presence of such protein with PCNA (nuclear antigen of the proliferating cells), which is a feature of the proliferating cells. The results show that p63 is not present in the replicating cells but in the stem cells, independent of their proliferative state.

As a result of the selection processes described above there are provided cell cultures mainly consisting of stem cells and able to regenerate corneal tissue in vitro. Furthermore, it is shown that such corneal tissue is capable advantageously of keeping its physiologic functions for at least 5 years after being grafted in the patient.

MODIFICATION OF THE FIBRIN SUBSTRATE

It is well-known that fibrin is obtained from the reaction of polymerization of fibrinogen induced by thrombin. This substance is a real sealant for cells that are going to form a continuous, homogeneous layer.

Such components are commercially known under the name of TISSUCOL (Baxter-Immuno, Vienna, Austria). As already mentioned, the protocol for preparing this commercial product is not adapted to the reconstruction in vitro of laminae of human epithelium corneae as such product is not transparent and elastic enough.

In order to overcome such problem, the preparation protocol has been modified in a suitable manner to obtain thrombin and fibrin solutions that allow a fibrin gel having the required flexibility and transparency to be provided upon their mixing.

This is accomplished by modifying the ionic strength of such solutions by adding salts such as sodium chloride and calcium chloride and modulating the polymerization reaction. Thus it is possible to determine exactly the chemical-physical characteristics of the final product. In particular, the fibrin gel obtained by such process has a sodium concentration between 0.5 and 0.001 millimoles and a chlorine concentration between 0.2 and 0.003 millimoles.

Both solutions for solubilizing thrombin and fibrin are then prepared by mixing NaCl, $CaCl_2$ and distilled $H_2O$.

The thrombin and fibrinogen packages of the commercial form TISSUCOL (Baxter-Immuno, Vienna, Austria) are defrosted in a thermostated bath at 37° C. Thereafter, an amount of the thrombin solution is transferred from the package to the test-tube and diluted by the previously prepared thrombin solubilization solution until a thrombin concentration between 2 and 5 OIU/ml is obtained. In the same way an amount of fibrin is transferred to a Petri dish and mixed with the solution prepared for the solubilization of the previously prepared fibrin.

Now the solutions prepared by this process are dispensed in a sterile milieu to a dish for bacteriology where the circular shape is obtained by confining the fibrin substrate within a ring with a little larger diameter than that of the human cornea in order to provide laminae of human epithelium corneae fitting the ocular surface as well as possible and keeping a suitable size following on the graft and the consequent resorption of the fibrin layer substrate.

The ring is prepared by cutting the upper end of a 50 ml test-tube with a diameter between 20 and 40 mm at a height between 3 and 8.0 mm by a white-hot tungsten wire. The object obtained is then put into autoclave to be sterilized.

After gentle stirring to distribute the gel uniformly, the dish is kept in the sterile milieu up to a complete polymerization and stored at 4° C. for a time between 1 hour and 1 month.

The fibrin gel formed as a result of the polymerization reaction has the desired chemical-physical characteristics and is characterized in that it includes sodium in a concentration between 0.5 and 0.001 millimoles and chlorine in a concentration between 0.2 and 0.003 millimoles to provide a final 0.6 ml gel amount.

The fibrin layer in the form of gel obtained by this process has a thickness between 50 and 300 microns and a diameter between 15 and 40 mm and is elastic and transparent.

RECONSTRUCTION OF LAMINAE OF EPITHELIUM CORNEAE IN VITRO

Figure 5:
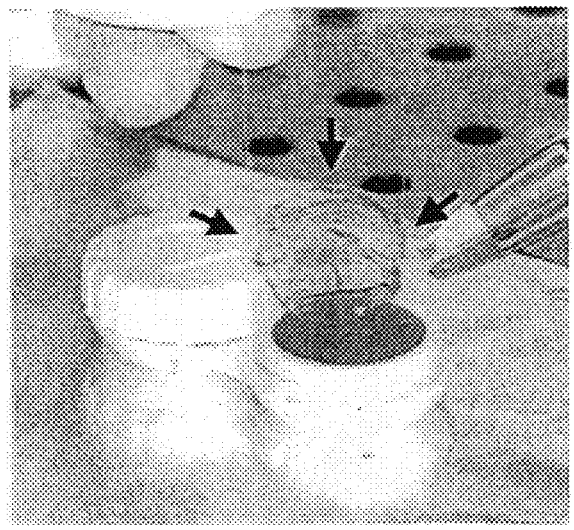
FIG. 5 shows the lamina of epithelium corneae obtained in vitro.

Limbar keratinocytes cultures obtained as previously described are treated by trypsin and put on a dish on the fibrin ring with cellular density between $2.5 \times 10^4$ cells/$cm^2$ and $1 \times 10^5$ cells/$cm^2$ in the presence of a nutritive layer of 3T3-J2 cells (murine embryonal fibroblasts) subjected to lethal radiations and having the characteristics described above. Upon confluence the epithelial layers obtained on the modified fibrin substrate are washed by Dulbecco Modified Eagle's Medium (DMEM) including glutamine, penicillin and streptomycin and stored into a case for contact lenses (Bausch and Lomb) in the presence of DMEM, as shown in FIG. 5. The lamina of human limbar-corneal epithelium obtained by this process is ready to use in therapy.

EXAMPLE

Cellular cultures from confluence biopsies are removed from culture flasks with Dispase II (Green, H., et al., 1979, Proc. Natl. Acad. Sci. USA, 76, 5665–5668), fixed in formaldehyde (4% in PBS) for 12 hours at 4° C. and put into paraffin. The sections are coloured by haematoxylin-eosin or specific monoclonal antibodies for cytokeratin 3 (AE5 mAB; DAKO) and cytokeratin 19 (RCK108 mAB; DAKO). The same coloration is also made in a maximum time of 24 hours by using an amount of cells removed from a non-confluence culture, cytocentrifuged on a glass and dried.

The specific cytokeratin 3 antibody bound to substrate is identified by using the HRP-dextran-anti-mouse complex (EnVision Plus/HPR system DAKO) and 3,3'-diaminobenzidine tetrachlorate (FAST DAB; Sigma Chemical Co.) as chromogen.

The specific cytokeratin 19 antibody bound to substrate is identified by using the alkaline phosphatase-dextran-anti-mouse complex (EnVision Plus/HPR system DAKO) and Fast rED TR/Naphtol AS-MX (FAST Red; Sigma Chemical Co.) as chromogen.

The presence of corneal stem cells is calculated by clonal analysis and then single cells isolated by microscope are inoculated in wells containing a nutritive layer of 3T3-J2 cells (murine embryonal fibroblasts) (Rochat, A. et al., 1994, Cell, 76, 1063–1073) cultivated up to the tenth passage and amplified until a proportion of max. 1:10 is obtained. After 7 days the clones are identified by microscope, whereupon their size is measured and they are transferred onto a dish containing a layer of 3T3-J2 cells. After 12 days the content of the dish is fixed by rhodamine B.

The clonal type is determined by analysing the proportion of abortive colonies (Barrandon, Y. and Green, H., 1987, Proc. Natl. Acad. Sci. USA, 84, 2302–2306).

The results obtained by clonal analysis are confirmed by the analysis conducted by using protein p63.

Cellular cultures both from confluence biopsies and previously identified clones are removed from the culture jars with Dispase II (Green, H., et al., 1979, Proc. Natl. Acad. Sci. USA, 76, 5665–5668), fixed in formaldehyde (4% in PBS) for 30 minutes at room temperature and put into paraffin.

The treated cells or an amount thereof removed from a non-confluence culture, cytocentrifuged on a glass and fixed after 24 hours with a mixture of oxygen peroxide and methanol for 5 minutes at 20° C. are coloured with specific monoclonal antibodies for p63 (given by Frank Kckeon) and a specific antibody for PCNA (nuclear antigen of the proliferating cells) (Santa Cruz Biotechnology) according to known techniques (Yang, A. et al., 1999, Nature, 398, 714–718; Parsa, R. et al., 1999, J. Invest. Dermatol., 113, 1099–1105; Bravo, R. et al., 1987, Nature, 326, 515–517). The cells are extracted for the blotting with a RIPA buffer (0.15 mM NaCl/0.05 mM Tris HCl, pH 7.2/1% Triton X-100/1% sodium deoxycholate/0.1% SDS), as already described by the same inventor (Dellambra, E. et. al., 2000, J. Cel. Biol., 149, 117–1129) and like specimens are subjected to electrophoresis on a gel of polyacrylamide/SDS and transferred to filters of polyvynilidenedifluoride (PVDF) (Immobilon-P, Millipore). The immunologic reactions are executed as described above and the antibodies bound to the filter are detected by chemiluminescence with ECL (Amersham Pharmacia).

As described above the cell cultures obtained by the above process are formed by 95% corneal stem cells.

The solution for solubilizing thrombin is prepared by mixing 11 ml of 10% NaCl with 1 ml of 100 mM $CaCl_2$ in 88 ml distilled $H_2O$. Likewise the solution for solubilizing fibrin is prepared by mixing 1038 microliters of 10% NaCl, 1.74 ml of 0.9% NaCl, and 108 microliters of 100 mM $CaCl_2$ in 2914 microliters distilled $H_2O$. The packages of thrombin and fibrinogen are kept in a thermostated bath at 37° C. until they are completely defrosted. Thereafter, 0.5 ml of the thrombin solution is transferred from the package to a test-tube and subjected to dilution with 4.5 ml of the previously prepared thrombin solubilizing solution, whereupon 1.5 ml of such solution is further diluted with 25 ml of the thrombin solubilizing solution to obtain a thrombin concentration of 3 OIU/ml. In the same way 5 ml fibrin is transferred onto a Petri dish and mixed with 5.8 ml of the previously prepared fibrin solubilizing solution.

Therefore, 0.3 ml of each above solution are dispensed in a sterile milieu onto a dish for bacteriology where the ring prepared by cutting the upper end of a 50 ml test-tube with a diameter of 30 mm at a height of 8.0 mm by a white-hot tungsten wire has been placed, and then put into autoclave.

After gentle stirring to distribute the gel uniformly, the dish is kept in the sterile milieu up to a complete polymerization and stored at 4° C. for a time between 1 hour and 1 month.

The fibrin gel formed as a result of the polymerization reaction is characterized in that it includes sodium in a concentration between 0.08 and 0.16 millimoles and an optimum amount of chlorine in a concentration between 0.03 and 0.01 millimoles. Just because of the precise ratio between sodium and calcium chlorides said gel has the desired chemical-physical characteristics.

The fibrin gel layer obtained by this process has a thickness of 100 microns and a diameter of 33 mm and is elastic and transparent. Finally the laminae of corneal epithelium ready to be grafted are obtained by treating with trypsin the cultures of limbar keratinocytes prepared as described above with Dispase II and putting them on a dish on the fibrin ring with cell density between $2.5 \times 10^4$ cells/cm$^2$ and $1 \times 10^5$ cells/cm$^2$ in the presence of a nutritive layer of 3T3-J2 cells. Upon confluence the epithelial layers on the fibrin substrate are washed by Dulbecco Modified Eagle's Medium (DMEM) including 4 mM glutamine, 50 IU/ml penicillin and 50 µg/ml streptomycin and stored into a case for contact lenses (Bausch and Lomb) in the presence of DMEM.

Laminae of human corneal epithelium reconstructed by this process have been tested clinically on 18 patients suffering from loss of sight due to severe burns caused by chemical agents, 11 of which were affected by total loss of limbus and 3 patients were affected by severe depletions of the limbar status. The graft of reconstructed corneae in vitro gave positive results in 14 over 18 patients. More exactly, the corneal epithelium is completely recovered after about 7 days, all symptoms connected to the inflammatory and vascularization processes regress after 3–4 weeks, and the cornea surface looks covered by a smooth, transparent epithelium after one month. Finally, the cornea epithelium recovers its natural characteristics as a whole after 12–24 months and the sharpness of sight of the patients becomes normal again in case of non-severe damages, while such method allows the so-called perforating keratoplasty to be successfully executed and the sight to be later recovered in case of severe damages. In addition, such method allows heterograft rejections to be avoided in case the patient has retained 1 mm of limbus region at least in one of his eyes.

In conclusion, the present invention permits laminae of human epithelium corneae which can be used in grafts to be easily obtained in vitro with size and transparency quite similar to human ones. Furthermore, the fibrin substrate prepared by this method helps the graft because of its prompt resorption without any allergic reaction in the patient. In addition, as mentioned above, said corneal tissue is capable of keeping its physiologic functions for at least 5 years after being grafted in the patient.

What is claimed is:

1. A method of producing laminae of human epithelium corneae in vitro, characterized in that the following steps are provided:
    a) selecting limbar stem cells having the capacity of regenerating the corneal tissue in vitro,
    b) preparing a fibrin substrate able to allow the limbar cells to grow for the production of said laminae of epithelium corneae that are transparent and elastic and have a predetermined thickness such as to allow them to be metabolized after being grafted,
    c) preparing limbar cornea cell cultures in vitro on said substrate within a ring compatible with the size of the human cornea.

2. The method of producing laminae of human epithelium corneae in vitro according to claim 1, characterized in that the selection of the limbar stem cells is obtained by clonal analysis and the use of specific genetic markers such as keratin 19, keratin 12, keratin 3, and protein p63.

3. The method of producing laminae of human epithelium corneae in vitro according to claim 1, characterized in that step b) provides that fibrin substrate is modified by adding sodium and calcium chlorides to the solutions for solubilizing thrombin and fibrinogen in order to modulate the polymerization reaction to provide transparency and elasticity.

4. The method of producing laminae of human epithelium corneae in vitro according to claim 3, characterized in that the fibrin substrate in the form of gel with a size compatible with the human cornea includes sodium in a concentration between 0.5 and 0.001 millimoles, and chlorine in a concentration between 0.2 and 0.003 millimoles.

5. The method of producing laminae of human epithelium corneae in vitro according to claim 3, characterized in that 0.6 ml of fibrin gel necessary for producing corneae with a size compatible to the human corneae includes sodium in a concentration between 0.08 and 0.16 millimoles and cholorine in a concentration between 0.03 and 0.01 millimoles.

6. The method of producing laminae of human epithelium corneae in vitro according to claim 1, characterized in that the fibrin substrate has a thickness between 50 and 300 microns.

7. The method of producing laminae of human epithelium corneae in vitro according to claim 1, characterized in that the fibrin substrate has a thickness of 100 microns.

8. The method of producing laminae of human epithelium corneae in vitro according to claim 1, characterized in that the cells are caused to grow on the modified fibrin substrate within a ring with a diameter between 15 and 40 mm and a height between 3 and 8.0 mm.

9. The method of producing laminae of human epithelium corneae in vitro according to claim 1, characterized in that the cells are caused to grow on the modified fibrin substrate within a ring with a diameter of 33 mm and a height between 3 and 8.0 mm.

10. The method of producing laminae of human epithelium corneae in vitro according to claim 1, characterized in that the corneae produced by such a method have a size similar to the human cornea.

11. The method of producing laminae of human epithelium corneae in vitro according to claim 1, characterized in that the corneae produced by such a method have the same transparency and function as the human cornea, and keep such characteristics after the graft.

12. The method of producing laminae of human epithelium corneae in vitro according to claim 1, characterized in that the corneae produced by such a method can be used in drafts for treating pathologies caused by the partial or total loss of limbus.

* * * * *